United States Patent
Shia et al.

(10) Patent No.: US 11,950,920 B2
(45) Date of Patent: Apr. 9, 2024

(54) DEVICE AND METHOD FOR ESTIMATING BREAST IMPLANT VOLUME

(71) Applicant: CHANGHUA CHRISTIAN MEDICAL FOUNDATION CHANGHUA CHRISTIAN HOSPITAL, Changhua County (TW)

(72) Inventors: Wei-Chung Shia, Changhua County (TW); Dar-Ren Chen, Changhua County (TW)

(73) Assignee: CHANGHUA CHRISTIAN MEDICAL FOUNDATION CHANGHUA CHRISTIAN HOSPITAL, Changhua County (TW)

( * ) Notice: Subject to any disclaimer, the term of this patent is extended or adjusted under 35 U.S.C. 154(b) by 1214 days.

(21) Appl. No.: 16/210,045

(22) Filed: Dec. 5, 2018

(65) Prior Publication Data

US 2019/0167183 A1   Jun. 6, 2019

(30) Foreign Application Priority Data

Dec. 5, 2017   (TW) .................................. 106142592

(51) Int. Cl.
*A61B 5/00* (2006.01)
*A61B 5/107* (2006.01)
*A61B 34/10* (2016.01)
*A61B 90/00* (2016.01)
*A61F 2/12* (2006.01)
*G16H 50/00* (2018.01)

(52) U.S. Cl.
CPC ............ *A61B 5/4312* (2013.01); *A61B 5/107* (2013.01); *A61B 5/1073* (2013.01); *A61B 34/10* (2016.02); *A61B 90/06* (2016.02); *A61B 2034/108* (2016.02); *A61B 2090/063* (2016.02); *A61F 2/12* (2013.01); *G16H 50/00* (2018.01)

(58) Field of Classification Search
CPC ..... A61B 5/4312; A61B 5/107; A61B 5/1073; A61B 34/10; A61B 90/06; A61B 2034/108; A61B 2090/063; A61F 2/12; G16H 50/00; G16H 20/40; G16H 50/50
See application file for complete search history.

(56) References Cited

PUBLICATIONS

Yip, Jia Miin MBBS*; Mouratova, Naila MBBS*; Jeffery, Rebecca M. BMBS, BSc (Kin)†; Veitch, Daisy E.‡; Woodman, Richard J. PhD, MBiostat†; Dean, Nicola R. PhD, FRACS (Plas)* Accurate Assessment of Breast vol. Annals of Plastic Surgery: Feb. 2012—vol. 68—Issue 2—p. 135-141 (Year: 2012).*

(Continued)

*Primary Examiner* — Bill Thomson
*Assistant Examiner* — Zainab Mohammed Aldarraji
(74) *Attorney, Agent, or Firm* — WPAT, P.C

(57) ABSTRACT

A device for estimating breast implant volume is provided, which may include an input interface and a processing circuit. A numerical value may be inputted in to the input interface. The processing circuit may calculate the estimation value of breast implant volume according to a linear model and the numerical value. The processing circuit may multiply the numerical value by a coefficient to generate a product, and add a constant to the product to generate the estimation value of breast implant volume, wherein the numerical value may be a breast sample weight or a breast size.

10 Claims, 6 Drawing Sheets

(56) References Cited

PUBLICATIONS

Utsunomiya H, Kusano T, Sato N, Yoshimoto S. Estimating Implant Volume and Mastectomy—Specimen Volume by Measuring Breast Volume With a 3-Dimensional Scanner. Ann Plast Surg. Jul. 2017;79(1):79-81 (Year: 2017).*

Peter R. Bloomfield, Least Absolute Deviations Curve-Fitting, 1977, Siam Journal on Scientific and Statistical Computing, vol. 1, pp. 290-301 (Year: 1977).*

* cited by examiner

DEVICE AND METHOD FOR ESTIMATING BREAST IMPLANT VOLUME

CROSS REFERENCE TO RELATED APPLICATION

This application also claims priority to Taiwan Patent Application No. 106142592 filed in the Taiwan Patent Office on Dec. 5, 2017, the entire content of which is incorporated herein by reference.

TECHNICAL FIELD

The present disclosure relates to a device for estimating implant volume, in particular to a device for estimating breast implant volume. The present disclosure further relates to the method of the device for estimating breast implant volume.

BACKGROUND

Compared with conventional mastectomy, nipple sparing mastectomy (NSM) has many advantages better than conventional mastectomy; thus, nipple sparing mastectomy gradually attracts more attention and people's acceptance for nipple sparing mastectomy also gradually increases. However, a doctor should estimate the breast implant volume of a patient and then reconstructs the breasts of the patient after the patent undergoes nipple sparing mastectomy.

Generally speaking, the doctor can estimate the breast implant volume according to the weight of the breast tissue cut off. However, there are no absolute correlation between the implant volume and the cut specimen weight and might variate due to the differ condition. If the doctor lacks in experience, the doctor cannot correctly estimate the ideal breast implant volume only according to the breast tissue cut off. Besides, not even an experienced doctor can correctly estimate the ideal breast implant volume.

The other method frequently-used to estimate breast implant volume is sizer; the doctor can estimate the breast implant volume by the silicone breast implants or saline bags with different sizes during the surgery. However, sizer will significantly increase the time of the surgery, and may damage the patient or incur infection. In addition, sizer cannot also correctly estimate the ideal breast implant volume.

As described above, there is no a proper method capable of correctly estimating the ideal breast implant, so it is very inconvenient to prepare materials for nipple sparing mastectomy and results in a lot of waste, which significantly increases the cost of the breast reconstruction surgery.

Thus, it has become an important issue to provide a breast implant estimation technique capable of improving the various shortcomings of the prior art.

SUMMARY

The present disclosure is related to a device for estimating breast implant volume. In one embodiment of the disclosure, the device for estimating breast implant volume includes an input interface and a processing circuit. A numerical value is inputted in to the input interface. The processing circuit calculates the estimation value of breast implant volume according to a linear model and the numerical value. The processing circuit multiplies the numerical value by a coefficient to generate a product, and adds a constant to the product to generate the estimation value of breast implant volume, wherein the numerical value is a breast sample weight or a breast size.

In a preferred embodiment, the breast sample weight is the weight of breast tissue cut off.

In a preferred embodiment, when the numerical value is the breast sample weight, the coefficient is 0.6302~0.6519.

In a preferred embodiment, when the numerical value is the breast sample weight, the constant is 58.29~66.07.

In a preferred embodiment, the breast size is a volume measurement value measured by the craniocaudal projection view of the mammography.

In a preferred embodiment, when the numerical value is the breast size, the coefficient is 0.3742~0.3963.

In a preferred embodiment, when the numerical value is the breast size, the constant is 96.97~107.5.

In a preferred embodiment, the device further includes a memory circuit, wherein the memory circuit saves statistics data and the processing circuit establishes the linear model according to the statistics data.

In a preferred embodiment, the processing circuit establishes the linear model by processing the statistics data via one or the combination of curve fitting and linear regression model.

In a preferred embodiment, the processing circuit optimizes the linear model via one or the combination of least absolute residuals or robust regression scheme.

The present disclosure is further related to a method for estimating breast implant volume. In one embodiment of the disclosure, the method for estimating breast implant volume includes the following steps: providing a numerical value, wherein the numerical value is a breast sample weight or a breast size; providing a linear model and multiplying the numerical value by a coefficient according to the linear model to generate a product; and adding a constant to the product to generate the estimation value of breast implant volume.

In a preferred embodiment, the breast sample weight is the weight of breast tissue cut off.

In a preferred embodiment, when the numerical value is the breast sample weight, the coefficient is 0.6302~0.6519.

In a preferred embodiment, when the numerical value is the breast sample weight, the constant is 58.29~66.07.

In a preferred embodiment, the breast size is the volume measurement value measured by the craniocaudal projection view of the mammography.

In a preferred embodiment, when the numerical value is the breast size, the coefficient is 0.3742~0.3963.

In a preferred embodiment, when the numerical value is the breast size, the constant is 96.97~107.5.

In a preferred embodiment, the method further includes the following step: providing statistics data and establishing the linear model according to the statistics data.

In a preferred embodiment, the method further includes the following step: establishing the linear model by processing the statistics data via one or the combination of curve fitting and linear regression model.

In a preferred embodiment, the method further includes the following step: optimizing the linear model via one or the combination of least absolute residuals or robust regression scheme.

The device and method for estimating breast implant volume include the following advantages:

(1) In one embodiment of the present disclosure, the device for estimating breast implant volume can correctly and swiftly calculate the estimation volume of breast implant volume via a linear model and the breast sample weight or the breast size of a patient, so can effectively reduce the cost of the breast reconstruction surgery.

(2) In one embodiment of the present disclosure, the device for estimating breast implant volume can correctly and swiftly calculate the estimation volume of breast implant volume via the linear model and the breast sample weight or the breast size of the patient, so will not result in damages to the patient and can reduce the incidence of infection.

(3) In one embodiment of the present disclosure, the device for estimating breast implant volume can be realized by a mobile device, which is very convenient in use.

(4) In one embodiment of the present disclosure, the device for estimating breast implant volume can update the statistics data, so can keep optimizing the linear model for estimating breast implant volume; therefore, the accuracy of the device for estimating breast implant volume can continuously increase.

(5) In one embodiment of the present disclosure, the design of the device for estimating breast implant volume is very simple, so can achieve the desired technical effects without significantly increasing cost; therefore, the device can achieve high commercial value.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
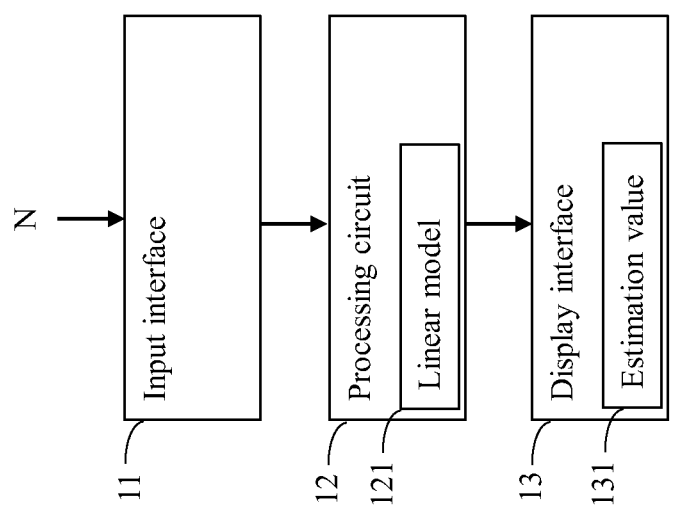
FIG. 1 is a block diagram of a device for estimating breast implant volume of a first embodiment in accordance with the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing. It should be understood that, when it is described that an element is "coupled" or "connected" to another element, the element may be "directly coupled" or "directly connected" to the other element or "coupled" or "connected" to the other element through a third element. In contrast, it should be understood that, when it is described that an element is "directly coupled" or "directly connected" to another element, there are no intervening elements.

Please refer to FIG. 1, which is a block diagram of a device for estimating breast implant volume of a first embodiment in accordance with the present disclosure. As shown in FIG. 1, the device 1 for estimating breast implant volume includes an input interface 11, a processing circuit 12 and a display interface 13; in one embodiment, the device 1 for estimating breast implant volume may be a mobile device, such as smart phone, smart watch, tablet computer, personal digital assistant (PDA), notebook computer, etc.

A user can input a numerical value N into the input interface 11; in one embodiment, the input interface 11 may be a touch screen or other similar devices.

The processing circuit 12 is connected to the input interface 11 and calculates the estimation value 131 for a patient according to a linear model 121 and the numerical value N; in one embodiment, the processing circuit 12 may be a central processing unit (CPU), a microcontroller unit (MCU) or other similar devices.

The processing circuit 12 multiplies the numerical value N by a coefficient according to the linear model 121 to generate a product, and then adds a constant to the product to generate the estimation value 131 of breast implant volume; in the embodiment, the numerical value N may be the breast sample weight, which is the breast tissue cut off from the patient; alternatively, the numerical value N may be the breast size, which the volume measurement value measured by the craniocaudal projection view (CC view) of full-field digital mammography (FFDM); in another embodiment, the numerical value N may be other different data.

The display interface 13 is connected to the processing circuit 12 and displays the estimation value 131 as the reference for the user (e.g. a doctor); in one embodiment, the display interface 13 may be an LCD or other similar devices.

More specifically, the linear model 121 adopted by the processing circuit 12 can be expressed by Equation (1), as follows:

$$y = Ax + B \tag{1}$$

In Equation (1), y stands for the estimation value 131 of breast implant volume; x stands for the numerical value N (i.e. the breast sample weight or the breast size) inputted in the input interface 11; A stands for the coefficient; B stands for the constant.

When the numerical value N is the breast sample weight, A (the coefficient) is 0.6302~0.6519 and B (the constant) is 58.29~66.07; in one embodiment, A (the coefficient) may be about 0.641 and B (the constant) may be about 62.18.

When the numerical value N is the breast size, A (the coefficient) is 0.3742~0.3963 and B (the constant) is 96.97~107.05; in one embodiment, A (the coefficient) may be about 0.3853 and B (the constant) may be about 102.2.

The above linear model 121 can be obtained by the statistics model established according to a large amount of statistics data, so is of high reliability; therefore, the device 1 for estimating breast implant volume can accurately calculate the estimation value 131 of breast implant volume.

As described above, the device 1 for estimating breast implant volume can directly and accurately calculate the estimation value 131 of breast implant volume according to the breast sample weight or the breast size of the patient; thus, the user can directly input the breast sample weight or the breast size of the patient into the input interface 11 to swiftly and accurately calculate the estimation value 131 of breast implant volume, so the cost of the breast reconstruction surgery can be effectively reduced.

The embodiment just exemplifies the present disclosure and is not intended to limit the scope of the present disclosure; any equivalent modification and variation according to the spirit of the present disclosure is to be also included within the scope of the following claims and their equivalents.

Figure 2:
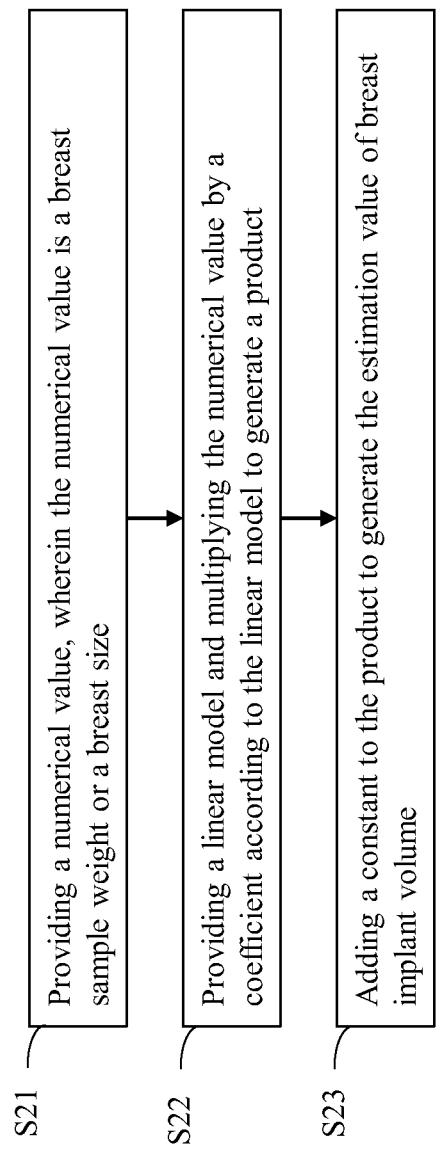
FIG. 2 is a flow chart of the first embodiment of the present disclosure.

Please refer to FIG. 2, which is a flow chart of the first embodiment of the present disclosure. The method of the device 1 for estimating breast implant volume includes the following steps:

Step S21: providing a numerical value, wherein the numerical value is a breast sample weight or a breast size.

Step S22: providing a linear model and multiplying the numerical value by a coefficient according to the linear model to generate a product.

Step S23: adding a constant to the product to generate the estimation value of breast implant volume.

Figure 3:
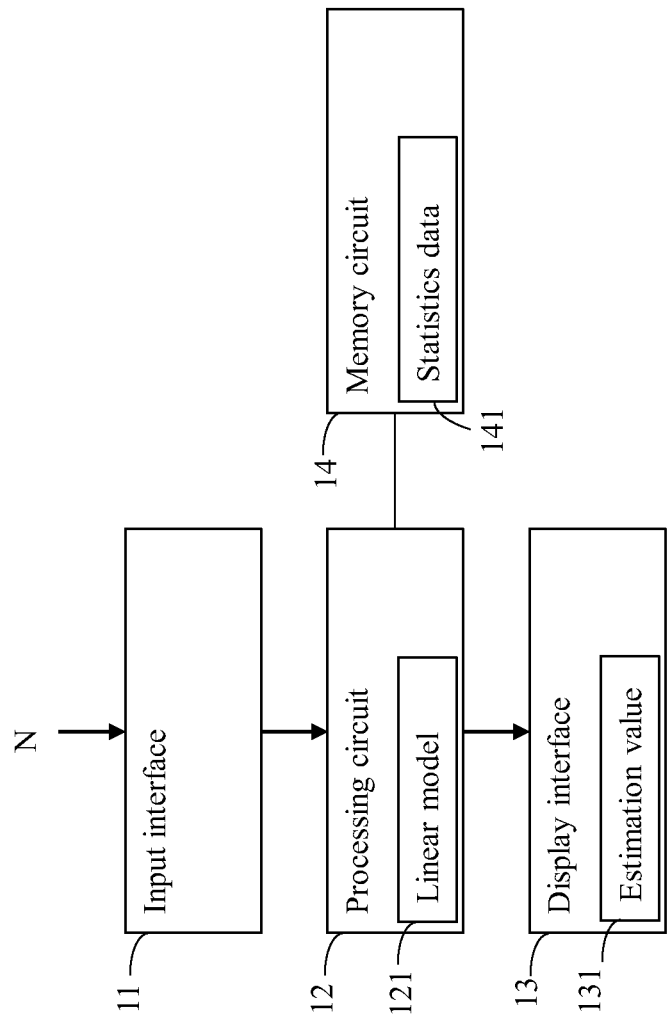
FIG. 3 is a block diagram of a device for estimating breast implant volume of a second embodiment in accordance with the present disclosure.

Please refer to FIG. 3, which is a block diagram of a device for estimating breast implant volume of a second embodiment in accordance with the present disclosure. As shown in FIG. 3, the device 1 for estimating breast implant volume includes an input interface 11, a processing circuit 12 and a display interface 13.

The above elements of the device 1 for estimating breast implant volume are similar to those of the previous embodiment, so will not be described herein again; the difference between the embodiment and the previous embodiment is that the device 1 for estimating breast implant volume of the embodiment further includes a memory circuit 14.

The memory circuit 14 is connected to the processing circuit 12 and saves the statistics data within a time period. The statistics data 141 includes the breast samples of a plurality of patients undergoing nipple sparing mastectomy and the volumes of the breast implants actually used by these patients; besides, the statistics data 141 can also include the breast sizes of these patients and the volumes of the breast implants actually used by these patients.

The processing circuit 12 establishes a linear model 121 according to the breast samples of these patients and the volumes of the breast implants actually used by these patients. Alternatively, the processing circuit 12 can also establish the linear model 121 according to the breast sizes of these patients and the volumes of the breast implants actually used by these patients. More specifically, the processing circuit 12 establishes the linear model 121 by using one or the combination of curve fitting and the linear regression model to process the statistics data 141, and then optimizes the linear model 121 via one or the combination of least absolute residuals and robust regression scheme.

As described above, the processing circuit 12 can establish the statistics model via a large amount of the statistics data 141 and the statistics analysis method, and further calculate the most appropriate linear model 121, so the linear model 121 can be of high reliability; therefore, the device 1 for estimating breast implant volume can accurately calculate the estimation value 131 of breast implant volume.

The embodiment just exemplifies the present disclosure and is not intended to limit the scope of the present disclosure; any equivalent modification and variation according to the spirit of the present disclosure is to be also included within the scope of the following claims and their equivalents.

Figure 4:
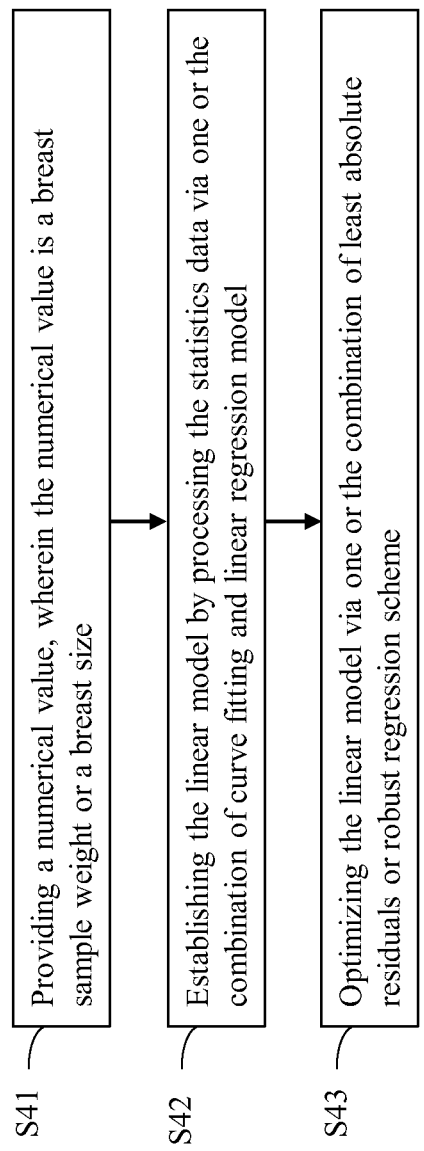
FIG. 4 is a flow chart of the second embodiment of the present disclosure.

Please refer to FIG. 4, which is a flow chart of the second embodiment of the present disclosure. The method of the device 1 for estimating breast implant volume includes the following steps:

Step S41: providing a numerical value, wherein the numerical value is a breast sample weight or a breast size.

Step S42: establishing the linear model by processing the statistics data via one or the combination of curve fitting and linear regression model.

Step S43: optimizing the linear model via one or the combination of least absolute residuals or robust regression scheme.

It is worthy to point out that there is no a proper method capable of correctly estimating the ideal breast implant, so it is very inconvenient to prepare materials for nipple sparing mastectomy and results in a lot of waste, which significantly increases the cost of the breast reconstruction surgery. On the contrary, according to one embodiment of the present disclosure, the device for estimating breast implant volume can correctly and swiftly calculate the estimation volume of breast implant volume via a linear model and the breast sample weight or the breast size of a patient, so can effectively reduce the cost of the breast reconstruction surgery.

Also, the currently available sizer cannot accurate estimate the ideal breast implant volume, and tends to damage patients and incur infection, which is not practical in use. On the contrary, according to one embodiment of the present disclosure, the device for estimating breast implant volume can correctly and swiftly calculate the estimation volume of breast implant volume via the linear model and the breast sample weight or the breast size of the patient, so will not result in damages to the patient and can reduce the incidence of infection.

Besides, according to one embodiment of the present disclosure, the device for estimating breast implant volume can be realized by a mobile device, which is very convenient in use.

Moreover, according to one embodiment of the present disclosure, the device for estimating breast implant volume can update the statistics data, so can keep optimizing the linear model for estimating breast implant volume; therefore, the accuracy of the device for estimating breast implant volume can continuously increase.

Furthermore, according to one embodiment of the present disclosure, the design of the device for estimating breast implant volume is very simple, so can achieve the desired technical effects without significantly increasing cost; therefore, the device can achieve high commercial value. As described above, the device for estimating breast implant volume definitely has an inventive step.

Figure 5:
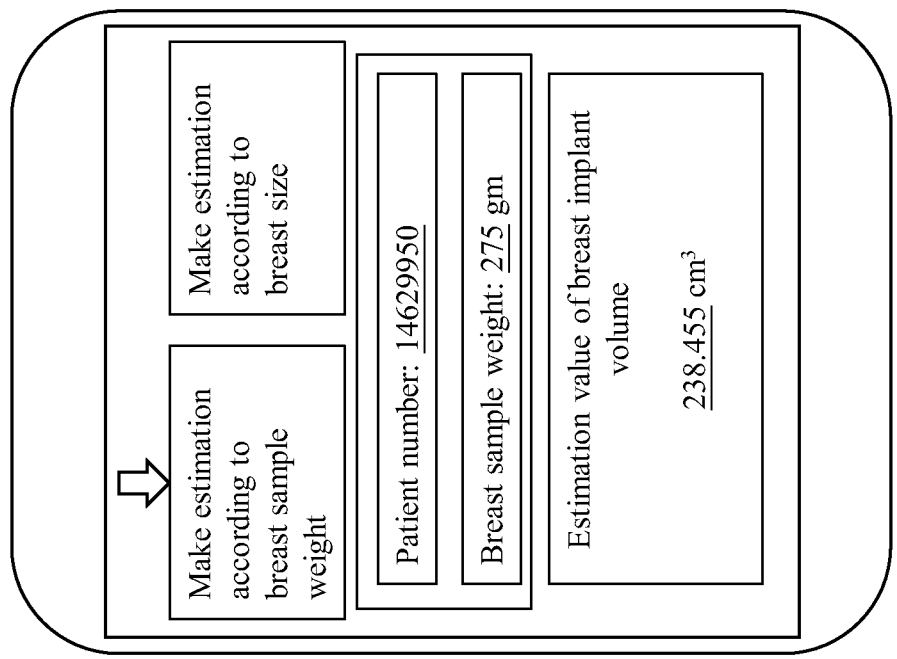
FIG. 5 is a first schematic view of a third embodiment in accordance with the present disclosure.
Figure 6:
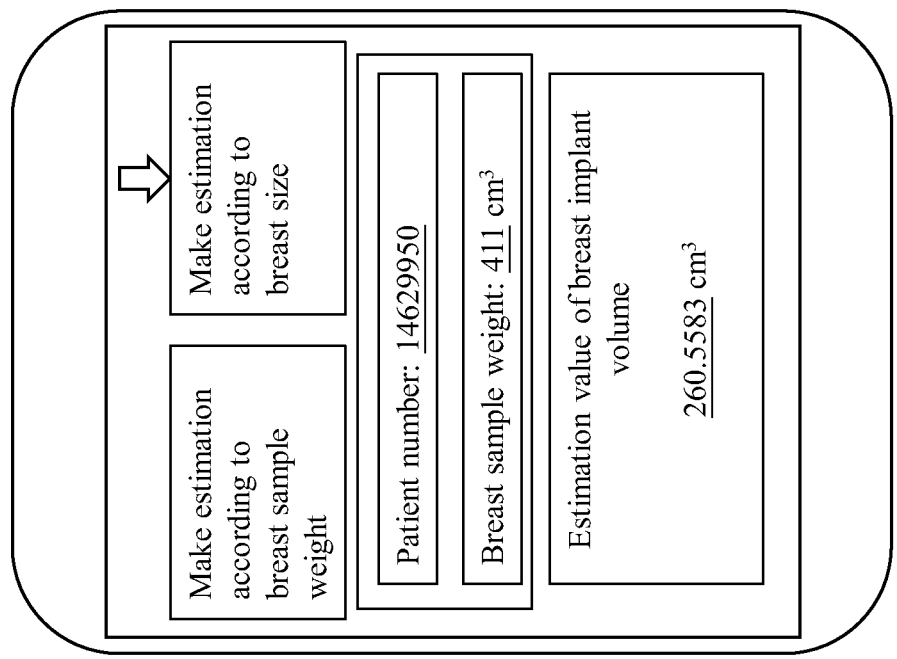
FIG. 6 is a second schematic view of the third embodiment in accordance with the present disclosure.

Please refer to FIG. 5 and FIG. 6, which are a first schematic view and a second schematic view of a third embodiment in accordance with the present disclosure. The embodiment illustrates the preferred usage situation of the device for estimating breast implant volume.

As described above, the device for estimating breast implant volume can be realized by a mobile device executing an application; the embodiment takes a smart phone 2 as an example, which can execute the application to realize the aforementioned functions of the device for estimating breast implant volume.

As shown in FIG. 5, the user can select making the estimation according to the breast sample weight of a patient; the user can input the number and the breast sample weight of the patient; then, the smart phone 2 can display the estimation value of breast implant volume is 238.455 $cm^3$.

As shown in FIG. 6, the user can select making the estimation according to the breast size of the patient; the user can input the number and the breast size of the patient; then, the smart phone 2 can display the estimation value of breast implant volume is 260.5583 cm$^3$.

In the embodiment, the breast implant volume actually used by the patient is 250 cm$^3$, which is very close to the above estimation values of breast implant volume.

The embodiment just exemplifies the present disclosure and is not intended to limit the scope of the present disclosure; any equivalent modification and variation according to the spirit of the present disclosure is to be also included within the scope of the following claims and their equivalents.

To sum up, according to one embodiment of the present disclosure, the device for estimating breast implant volume can correctly and swiftly calculate the estimation volume of breast implant volume via a linear model and the breast sample weight or the breast size of a patient, so can effectively reduce the cost of the breast reconstruction surgery.

Also, according to one embodiment of the present disclosure, the device for estimating breast implant volume can correctly and swiftly calculate the estimation volume of breast implant volume via the linear model and the breast sample weight or the breast size of the patient, so will not result in damages to the patient and can reduce the incidence of infection.

Besides, according to one embodiment of the present disclosure, the device for estimating breast implant volume can be realized by a mobile device, which is very convenient in use.

Moreover, according to one embodiment of the present disclosure, the device for estimating breast implant volume can update the statistics data, so can keep optimizing the linear model for estimating breast implant volume; therefore, the accuracy of the device for estimating breast implant volume can continuously increase.

Furthermore, according to one embodiment of the present disclosure, the design of the device for estimating breast implant volume is very simple, so can achieve the desired technical effects without significantly increasing cost; therefore, the device can achieve high commercial value.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A device for estimating breast implant volume, comprising:
    an input interface, configured to receive a numerical value;
    a memory circuit, configured to save a statistics data; and
    a processing circuit, configured to establish a linear model comprising a coefficient and a constant according to the statistics data and calculate an estimation value of breast implant volume according to the linear model and the numerical value, wherein the processing circuit establishes the linear model by processing the statistics data via one or a combination of a curve fitting and a linear regression model, and optimizes the linear model via a combination of a least absolute residuals or a robust regression scheme;
    wherein the processing circuit multiplies the numerical value by the coefficient to generate a product, and adds the constant to the product to generate the estimation value of breast implant volume; the numerical value is a breast sample weight or a breast size, wherein when the numerical value is the breast sample weight, the coefficient is a number from 0.6302 to 0.6519 and the constant is a number from 58.29 to 66.07.

2. The device of claim 1, wherein the breast sample weight is a weight of breast tissue cut off.

3. The device of claim 1, wherein the breast size is a volume measurement value measured by a craniocaudal projection view of a mammography.

4. The device of claim 3, wherein when the numerical value is the breast size, the coefficient is a number from 0.3742 to 0.3963.

5. The device of claim 4, wherein when the numerical value is the breast size, the constant is a number from 96.97 to 107.5.

6. A method for estimating breast implant volume, comprising:
    providing a statistics data;
    establishing a linear model comprising a coefficient and a constant by processing the statistics data via one or a combination of a curve fitting and a linear regression model;
    optimizing the linear model via one or a combination of a least absolute residuals or a robust regression scheme;
    providing a numerical value, wherein the numerical value is a breast sample weight or a breast size, wherein when the numerical value is the breast sample weight, the coefficient is a number from 0.6302 to 0.6519 and the constant is a number from 58.29 to 66.07;
    multiplying the numerical value by the coefficient according to the linear model to generate a product; and
    adding the constant to the product to generate an estimation value of breast implant volume.

7. The method of claim 6, wherein the breast sample weight is a weight of breast tissue cut off.

8. The method of claim 6, wherein the breast size is a volume measurement value measured by a craniocaudal projection view of a mammography.

9. The method of claim 8, wherein when the numerical value is the breast size, the coefficient is a number from 0.3742 to 0.3963.

10. The method of claim 9, wherein when the numerical value is the breast size, the constant is a number from 96.97 to 107.5.

* * * * *